(12) United States Patent
Henschke et al.

(10) Patent No.: US 8,497,374 B2
(45) Date of Patent: Jul. 30, 2013

(54) PROCESS FOR PREPARING AND PURIFYING BORTEZOMIB

(75) Inventors: Julian Paul Henschke, Summertown (AU); Aiping Xie, Jinan (CN); Xin Yan Huang, Jinan (CN); Yung Fa Chen, Chiali (TW)

(73) Assignee: Scinopharm Taiwan, Ltd., Tainan (TW)

( * ) Notice: Subject to any disclaimer, the term of this patent is extended or adjusted under 35 U.S.C. 154(b) by 138 days.

(21) Appl. No.: 13/105,964

(22) Filed: May 12, 2011

(65) Prior Publication Data

US 2012/0289699 A1  Nov. 15, 2012

(51) Int. Cl.
*C07D 241/02* (2006.01)

(52) U.S. Cl.
USPC .......................................... 544/406; 423/277

(58) Field of Classification Search
USPC .......................................... 423/277; 544/406
See application file for complete search history.

(56) References Cited

U.S. PATENT DOCUMENTS 7,714,159 B2   5/2010   Pickersgill et al.

FOREIGN PATENT DOCUMENTS

| WO | WO2008075376 | 6/2008 |
| WO | WO2009/004350 | 1/2009 |
| WO | WO2009/036281 | 3/2009 |

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*
M. A. Beenen, C. H. An, and J. A. Ellman, *J. Am. Chem. Soc.*, 2008, 130, 6910-6911.
A. V. Purandare, H. H Wan, N. Laing, K. Benbatoul, W. Vaccaro and M. A. Poss, *Bioorg. Med. Chem. Lett.* 2004, 4701-4704.
V. M. Dembitsky and M. Srebnik, *Tetrahedron*, 2003, 59, 579-593.
A. S. Ivanov, A. A. Zhalnina, S. V. Shishkov, *Tetrahedron*, 2009, 65, 7105-7108.

* cited by examiner

*Primary Examiner* — Douglas M Willis
(74) *Attorney, Agent, or Firm* — Enshan Hong; Kent H. Cheng; VLP Law Group LLP (57) ABSTRACT

A synthetic process for producing bortezomib comprising converting racemic boronic esters, such as the pinacol α-aminoboronic ester, into mixtures of diastereomers [6] by reaction with a suitably protected L-phenylalanine derivative (see Scheme 3), such as N—BOC-L-phenylalanine. The protecting group of the L-phenylalanine moiety is then removed, such as by reacting the diastereomers [6] with an acid, such as hydrochloric acid, to form a mixture of amine salt diastereomers [7] which is then subjected to conditions under which the desired diastereomer (R,S)-[7] is selectively isolated, such as by crystallization, chromatography or stereoselective hydrolysis. The separated desired diastereomer (R,S)-[7] is then converted into bortezomib or bortezomib anhydride.

7 Claims, 7 Drawing Sheets

FIG.1A

| Pos.[°2Th.] | Height[cts] | FWHM[°2Th.] | d-spacing[Å] | Rel.Int.[%] |
|---|---|---|---|---|
| 5.5552 | 190.19 | 0.1948 | 15.90904 | 1.80 |
| 6.7763 | 10545.75 | 0.1624 | 13.04469 | 100.00 |
| 8.3553 | 668.04 | 0.2598 | 10.58260 | 6.33 |
| 9.7528 | 148.57 | 0.2598 | 9.06915 | 1.41 |
| 10.0731 | 125.04 | 0.0974 | 8.78148 | 1.19 |
| 10.5939 | 172.20 | 0.1948 | 8.35090 | 1.63 |
| 11.7801 | 359.76 | 0.1948 | 7.51255 | 3.41 |
| 12.1046 | 385.60 | 0.1948 | 7.31190 | 3.66 |
| 13.1765 | 504.05 | 0.1948 | 6.71937 | 4.78 |
| 14.5966 | 159.52 | 0.2598 | 6.06868 | 1.51 |
| 15.9187 | 434.49 | 0.2273 | 5.56752 | 4.12 |
| 16.4870 | 423.64 | 0.3247 | 5.37687 | 4.02 |
| 18.2719 | 833.20 | 0.1299 | 4.85544 | 7.90 |
| 18.9823 | 745.66 | 0.2598 | 4.67532 | 7.07 |
| 19.4592 | 714.81 | 0.2273 | 4.56179 | 6.78 |
| 21.4176 | 476.55 | 0.5845 | 4.14890 | 4.52 |
| 22.8540 | 237.72 | 0.2598 | 3.89128 | 2.25 |
| 25.1684 | 398.18 | 0.2273 | 3.53845 | 3.78 |
| 26.4025 | 123.74 | 0.5196 | 3.37579 | 1.17 |

FIG.1B

| FIG.1A |
|---|
| FIG.1B |

PROCESS FOR PREPARING AND PURIFYING BORTEZOMIB

BACKGROUND OF THE INVENTION

Field of the Invention

Bortezomib (PS-341, Velcade®; N-(pyrazin-2-yl)carbonyl-L-phenylalanine-L-leucine boronic acid; (1R)-3-Methyl-1-[(2S)-3-phenyl-2-[(pyrazinylcarbonyl)amino]propanoyl]amino]butyl]boronic acid; CAS Registry Number: 179324-69-7) is an N-acylated dipeptide analogue of phenylalanyl-leucine in which a boronic acid functional group replaces the C-terminal carboxylic acid. It is a white to almost white crystalline powder and when appropriately formulated for injection is an anti-neoplastic agent and is a therapeutic proteosome inhibitor. In the US this active pharmaceutical ingredient (API) is approved for the treatment of multiple myeloma and mantle cell lymphoma.

Bortezomib is composed of three moieties that are fused together by two amide bonds. Two of these three units can be thought of as analogues of amino acids (viz., an α-aminoboronic acid and a pyrazinecarboxylic acid) and the third unit is a naturally occurring amino acid (viz., L-phenylalanine). Bortezomib possesses two chiral centres but is a single stereoisomer. One chiral centre exists within the α-aminoboronic acid moiety and the other exists within the naturally occurring amino acid, L-phenylalanine, moiety. In the solid state under anhydrous conditions, bortezomib can exist as a trimeric anhydride (trimeric boroxine), herein referred to as bortezomib anhydride. In the presence of water this can be hydrolysed to its monomeric boronic acid form.

SUMMARY OF THE INVENTION

First Embodiment

The chiral centre of the α-aminoboronic acid moiety cannot, however, be derived from a chiral pool since α-aminoboronic acids are not known to be naturally occurring. Instead, enantio-enriched α-aminoboronic acids in which the chiral centre is adjacent to the boron atom can be obtained by the use of chiral boron chemistry developed by Matteson, such as disclosed in U.S. Pat. No. 4,525,309 and a series of peer reviewed publications. Matteson's chemistry when used for chiral applications utilises a boronic ester comprising a chiral diol auxiliary (such as 1 S,2S,3R,5S)-(+)-2,3-pinanediol ((S)-(+)-pinanediol), for example) which upon reaction with the lithium salt (this salt can be prepared in situ or separately) of dichloromethane forms an α,α-dichloroboron ate complex, which the boron ate functional group is chiral. Due to induction provided by the chiral diol auxiliary, the boron ate complex undergoes a spontaneous and stereoselective internal rearrangement with displacement of one of the prochiral chloro substituents to generate an α-chloroboronic ester which possesses a newly generated chiral centre adjacent to the boron atom (See Scheme 1). This rearrangement of the boron ate complex is dramatically improved by catalysis with $ZnCl_2$ (see *J. Am. Chem. Soc.*, 1983, 105, 2077-2078). α-Chloroboronic esters can be converted into the aforementioned requisite α-aminoboronic acids, preferably protected as boronic esters, possessing useful high chiral purity by reaction with LiHMDS followed by desilylation and optional salt formation of the amino group). Altogether, this reaction sequence provides a 1-carbon homologation of the original carbon backbone of the B-alkyl portion of the boronic ester in addition to a stereoselectively appended amino group. Most typically the chiral auxiliary demonstrated for this reaction sequence is homochiral pinanediol, such as the (+)-enantiomer referred to as (S)-(+)-pinanediol, or the (−)-enantiomer referred to as (R)-(−)-pinanediol.

Scheme 1-Matteson chemistry utilizing pinanediol useful for preparing α-aminoboronic esters α,α-Dichloroboronate complex α-Chloroboronic ester α-Aminoboronic ester salt One drawback with this stereoselective approach to α-aminoboronic acid synthesis in an industrial setting is the relatively high cost of the chiral diol auxiliary, pinanediol. Further, the use of the chiral diol imposes other synthetic restrictions, such as order of installation of the alkyl group to be homologated (i.e., the R group and dichloromethyl substituent) into the boron ate complex, and the relatively more difficult hydrolysis step required to remove stereochemically hindered diol groups afterwards. Despite this U.S. Pat. No. 7,714,159B2, WO2009004350A1 and WO2009036281A2 disclose methods for the synthesis of bortezomib utilizing Matteson's chemistry in conjunction with (S)-(+)-pinanediol as the chiral auxiliary.

Although a chiral auxiliary, such as (S)-(+)-pinanediol, is required for chiral induction in the homologation step in the Matteson reaction sequence, a chiral auxiliary itself is not inherently required for the Matteson homologation step to proceed, and achiral diols can also be used (*Organometallics*, 1983, 2, 1529-1535). The inventors of the invention herein reasoned that the high cost of (S)-(+)-pinanediol could be circumvented in the synthesis of bortezomib by the use of a cheap, achiral diol to protect the boronic acid functional group. Since the use of an achiral diol auxiliary would not provide any stereochemical induction in the homologation step, a racemic product (that is, it would comprise equimolar amounts of each enantiomer) would be produced, which itself or a down stream synthetic derivative of it would require a classical resolution or other technique capable of separating the stereoisomers to be performed upon it.

Given that there was a need for a separation method that could separate the racemate, the inventors reasoned that one efficient approach would utilise the enantiopure API building block, L-phenylalanine as an intramolecular chiral resolving agent. L-phenylalanine or its derivatives could serve as a cost efficient in-process chiral resolving agent in this manner because i) it and its derivatives are cheap and are commercially available on large scales, and ii) it comprises part of the molecular structure of bortezomib itself. Therefore it was reasoned that its use would not be wasteful once the desired enantiomer of the racemate was separated because it would also be incorporated into the API itself.

Thus, a key characteristic of the invention herein useful for the synthesis of bortezomib is the use of a racemic diol α-aminoboronic ester salt, such as the pinacol derivative [5], as a key intermediate. This racemic key intermediate is derivatised by its reaction with L-phenylalanine to provide a mixture of diastereomers that are separated by crystallisation, or by chromatography, or by stereoselective hydrolysis.

The requisite racemic boronic esters, such as pinacol α-aminoboronic ester [5], are readily synthesized utilizing prior art chemistry disclosed by Matteson (e.g., see *Pure & Appl. Chem.*, 1985, 57, 1741-1748), as exemplified in Scheme 2.

Scheme 2

The racemic boronic esters, such as the pinacol α-aminoboronic ester [5], are then converted into mixtures of diastereomers [6] by reaction with a suitably protected L-phenylalanine derivative (See Scheme 3), such as N—BOC-L-phenylalanine. The protecting group of the L-phenylalanine moiety is then removed, such as by reacting the diastereomers [6] with an acid such as hydrochloric acid, to form a mixture of amine salt diastereomers [7] which is then subjected to conditions under which the desired diastereomer (R,S)-[7] is selectively isolated, such as by crystallisation, chromatography or stereoselective hydrolysis. The separated desired diastereomer (R,S)-[7] is then converted into bortezomib or bortezomib anhydride.

Scheme 3

In this invention the need for the use of an expensive chiral auxiliary such as (S)-(+)-pinanediol to induce stereoselectivity in the Matteson homologation reaction sequence is circumvented by the use of the naturally occurring and relatively cheap amino acid L-phenylalanine in protected form. In addition to being 7-10 times cheaper than (S)-(+)-pinanediol, unlike (S)-(+)-pinanediol which is liberated from the penultimate API precursor at the end of the synthesis of bortezomib following the methods of the prior art, the amino acid, L-phenylalanine, comprises part of the final API molecular structure.

This invention differs from those disclosed in U.S. Pat. No. 7,714,159B2, WO2009004350A1 and WO2009036281A2 which all rely on the use of the expensive chiral diol auxiliary (S)-(+)-pinanediol in conjunction with Matteson chemistry to obtain the requisite chirality.

DETAILED DESCRIPTION OF THE PRESENTLY PREFERRED EMBODIMENTS

In our preferred embodiment the racemic α-aminoboronic ester [5] is generated using the Matteson chemistry without the need for an expensive chiral auxiliary. Upon reaction of the racemic aminoboronic ester with BOC-L-phenylalanine, a 1:1 diastereomeric mixture of products (viz., (R,S)-[6] and (S,S)-[6] is obtained. Other protecting groups could be used instead of the BOC-protecting group, such as Alloc (allyloxy-carbonyl), Cbz (benzyloxy-carbonyl), Fmoc (9H-fluoren-9- ylmethoxycarbonyl), and Trityl (triphenylmethyl), DMTr ((dimethoxy)triphenylmethyl). The BOC-protecting group is preferred for the protection of phenylalanine because it can be removed under conditions in which the released amine is provided as a salt without a separate salt forming step being required. Using anhydrous HCl in an organic solvent to deprotect the BOC protecting group of [6] diastereomers, a ca. 1:1 diastereomeric mixture of amine hydrochloride salts of the formula (R,S)-[7] and (S,S)-[7] are generated (viz.,. Small changes in the ratio of this mixture can occur during other unit operations involving crystallisations or precipitations when the difference in solubility of the two diastereomers is different.

The inventors discovered that the individual diastereomers of diastereomeric mixtures of amine hydrochloride salts (R,S)-[7] and (S,S)-[7] can be separated from one another using the laboratory techniques A-C (see below) or using a combinations of those techniques. When operation A or B was used, the desired (R,S)-[7] diasteromer could be conveniently isolated in enriched form by filtration:

Separation operations:
A) fractional crystallisation.
B) reslurry/hydrolysis.
C) chromatography.
D) or combinations of any of the above three techniques.

The desired stereoisomer (R,S)-[7] could be selectively isolated as a solid by filtration of the solid/liquid mixture following crystallisation (operation A) of an approximately 1:1 diastereomeric mixture. Similarly, the desired stereoisomer (R,S)-[7] could be selectively isolated as a solid by filtration of the solid/liquid mixture following slurry/hydrolysis (operation B) of an approximately 1:1 diastereomeric mixture. Enrichment of (R,S)-[7] could also be accomplished by column chromatography (operation C) of the diastereomeric mixture. Operations A-C can be repeated and can be used in combination to increase the selectivity for the desired diastereomer (R,S)-[7].

One aspect of the preferred embodiment is fractional crystallisation (Operation A) of the diastereomeric mixture. For example, when a (R,S)-[7]/(S,S)-[7] mixture with a molar ratio of 1.50:1 was fractionally crystallised from i-BuOAc/EtOH (14:1, volume/volume), a 98.6% HPLC pure (R,S)-[7]/(S,S)-[7] mixture with a molar ratio of 4.16:1 was obtained as determined by HPLC analysis. Subsequent recrystallisations of this from i-BuOAc/EtOH provided a 96.7% HPLC pure (R,S)-[7]/(S,S)-[7] mixture with a molar ratio of 17.5:1. This molar ratio of the diastereomers of [7] was sufficiently enriched such that it could then be converted into bortezomib using methods described in the prior arts. Small amounts of the undesired diastereomer that were not completely removed at the [7] stage formed a diastereomer of bortezomib, however, this could be removed by crystallisation of bortezomib anhydride itself. Thus it can be seen that fraction crystallisation can be used to upgrade the diastereomeric mixture molar ratio of [7] to useful levels which can then be used for the synthesis of bortezomib as a substantially pure stereoisomer.

In another aspect of the preferred embodiment a slurry of a diastereomeric mixture of [7] in a wet organic solvent is stirred for a period of time. It was surprisingly discovered by the inventors that diastereomeric mixtures of (R,S)-[7]/(S,S)-[7] that were exposed to the atmosphere underwent a chemical change resulting in an increase in the molar ratio of diastereomeric the mixtures of (R,S)-[7]/(S,S)-[7], as determined by HPLC analysis. The longer that the samples were exposed to the atmosphere at ambient temperatures (about 15-35° C.), the greater the enrichment of (R,S)-[7] that occurred. Without being bound by theory it is believed that this phenomenon was due to absorption of water from the atmosphere and that the water mediated stereoselective hydrolysis of the undesired (S,S)-[7] boronic ester diastereomer. For example, diastereomeric mixtures of (R,S)-[7]/(S,S)-[7] with molar ratios of >4:1 could be prepared from approximately 1.3:1 mixtures of (R,S)-[7]/(S,S)-[7] (see Table 1).

TABLE 1

Enrichment of diastereomers by exposure to the atmosphere

| Weight (R,S)-[7]/(S,S)-[7]$^a$ | Time | Combined (R,S)-[7]/(S,S)-[7] HPLC purity | HPLC ratio of (R,S)-[7]/(S,S)-[7] |
|---|---|---|---|
| 10 mg | 24 h | 78.8% | 1.82:1 |
| 10 mg | 72 h | 80.7% | 2.00:1 |
| 9 mg | 240 h | 82.1% | 2.09:1 |
| 10 mg | 246 h | 82.6% | 2.65:1 |
| 9 mg | 264 h | 94.0% | 4.24:1 |
| 10 mg | 288 h | 95.3% | 4.32:1 |

$^a$Each entry represents a separate experiment.

The inventors discovered that this phenomenon was best harnessed and made synthetically useful by the steps of i) stirring a slurry of a diastereomeric mixture of [7] in a wet organic solvent for a period of time such that the undesired diastereomer (S,S)-[7] was eliminated from the mixture, and then ii) filtration of the slurry to isolate the diastereomerically enriched (R,S)-[7] as a solid. For [7], it was preferred that EtOAc was selected as the solvent. It was preferred that the EtOAc contained about 0.3% w/w of water, which was about 2 molar equivalents of water with respect to the diastereomeric mixture of [7]. In step i) it was preferred that the slurry mixture was stirred at ambient temperature for a period of time such that the (R,S)-[7] diastereomer was adequately enriched as determined by HPLC analysis of the undisclosed solid, before step ii) was performed. For example, a 1.3:1 molar ratio of a mixture of diastereomerics (R,S)-[7] and (S,S)-[7] was converted into a molar ratio of 7.0:1 of the same diastereomers, as determined by HPLC analysis, after stirring the slurry for 72 h at ambient temperature in 30 volumes of EtOAc containing 2.2 molar equivalents of water, with respect to the [7]. From Table 2, it can be see that the diastereomeric molar ratio of the mixture of (R,S)-[7] and (S,S)-[7] increased indicating an enrichment of the (R,S)-[7] diastereomer in the solid phase as the time of stirring the wet EtOAc slurry at ambient temperature was prolonged.

TABLE 2

Operation B

| Stirring Time | Isolated [7] ((R,S)-[7] + (S,S)-[7]) HPLC purity | Ratio of (R,S)-[7]/(S,S)-[7] |
|---|---|---|
| 2.5 h | 96.5% | 4.75:1 |
| 24 h | 96.3% | 5.80:1 |

TABLE 2-continued

| | Operation B | |
|---|---|---|
| Stirring Time | Isolated [7] ((R,S)-[7] + (S,S)-[7]) HPLC purity | Ratio of (R,S)-[7]/(S,S)-[7] |
| 72 h | 97.7% | 7.02:1 |
| 120 h | 97.0% | 6.77:1 |

Another aspect of the preferred embodiment is the use of column chromatography to separate the diastereomers (Operation C). For example, a molar ratio upgrade of a diastereomeric mixture of (R,S)-[7]/(S,S)-[7] starting with a molar ratio of 0.83:1 is transformed into a mixture with a molar ratio of 2.25 by column chromatography over silica gel using a mixture of i-PrOH and DCM as the eluent.

Figures 1, 1B:
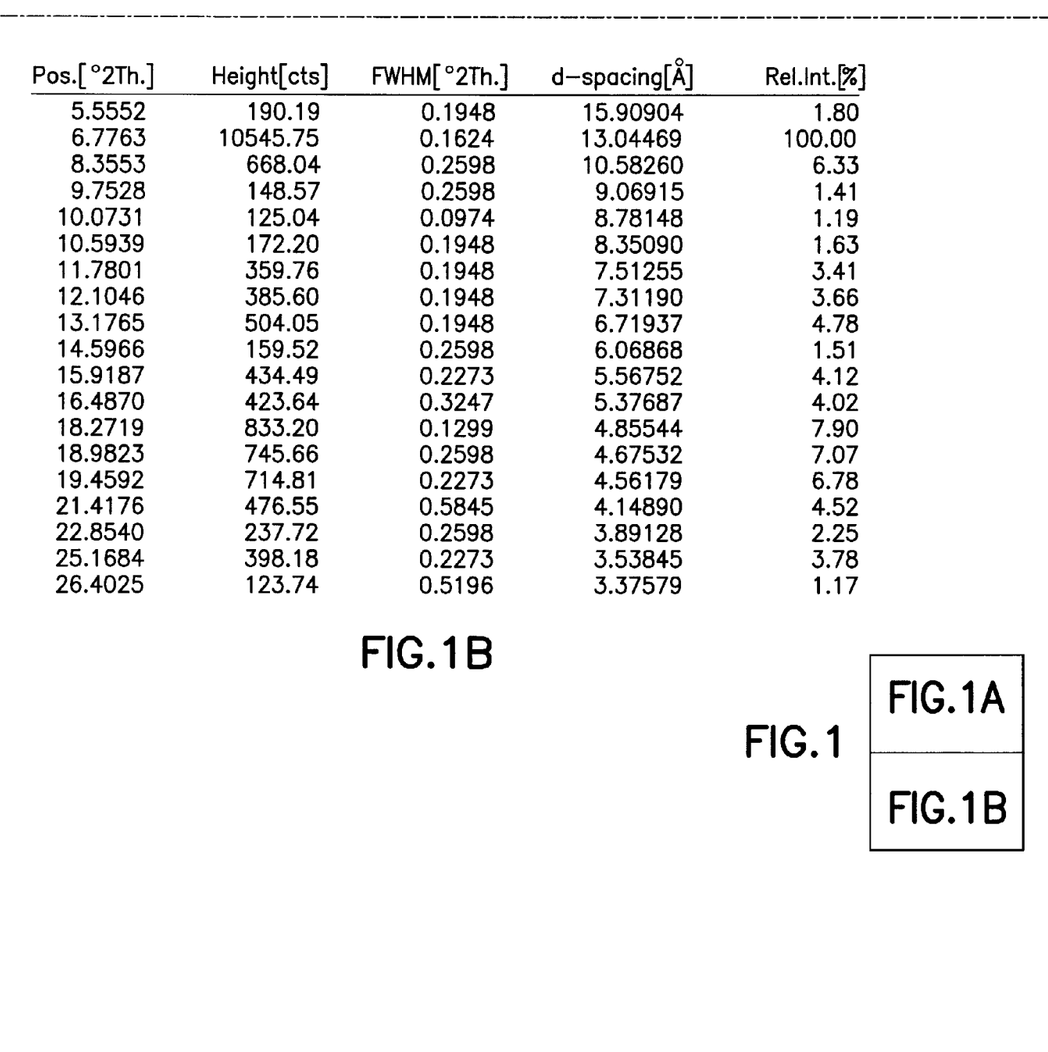
FIG. 1 shows the XRPD pattern and peak list of the crystalline form, Form C, isolated from slurry treatment in i-PrOH/MeCN
Figure 1A:
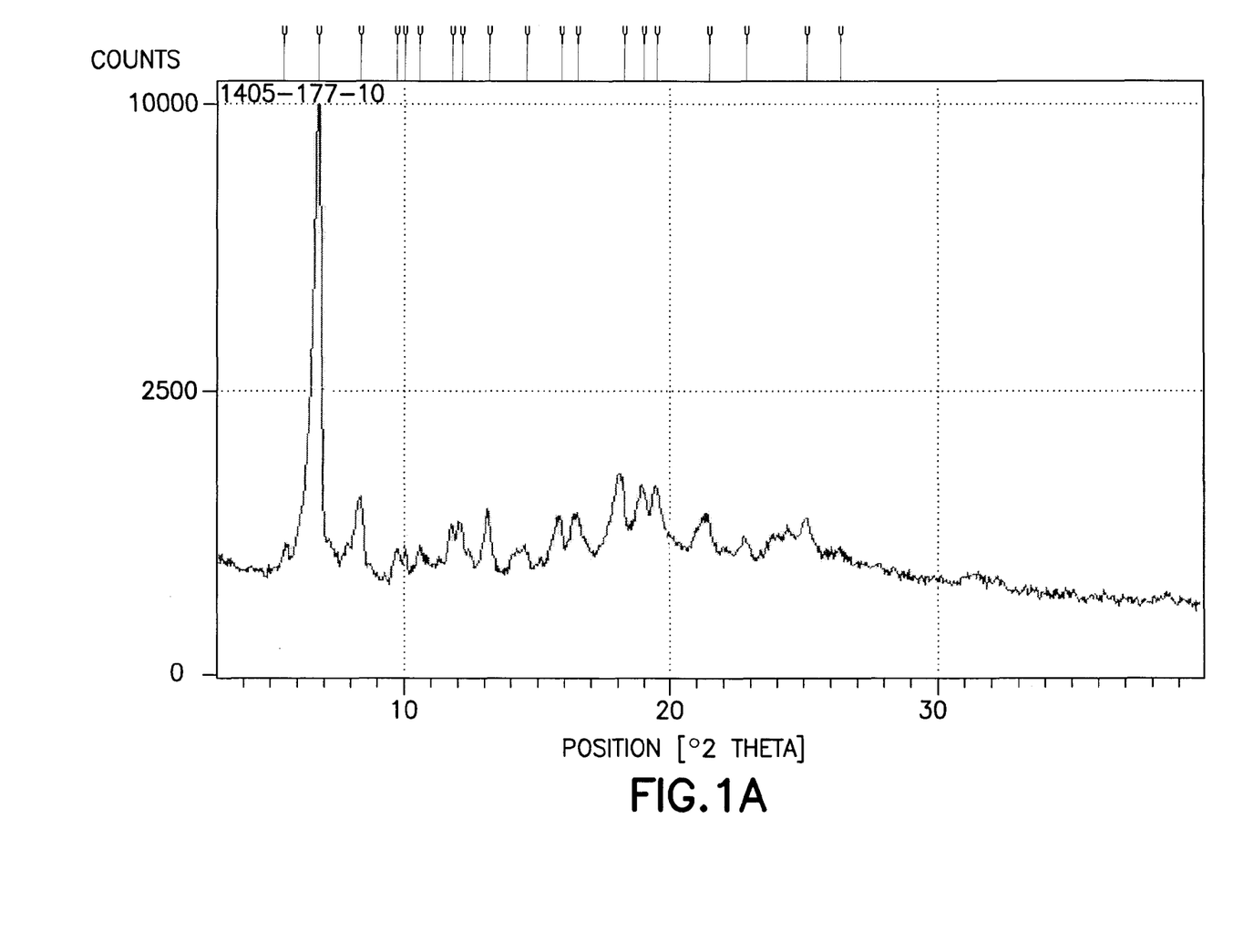
Figure 2:
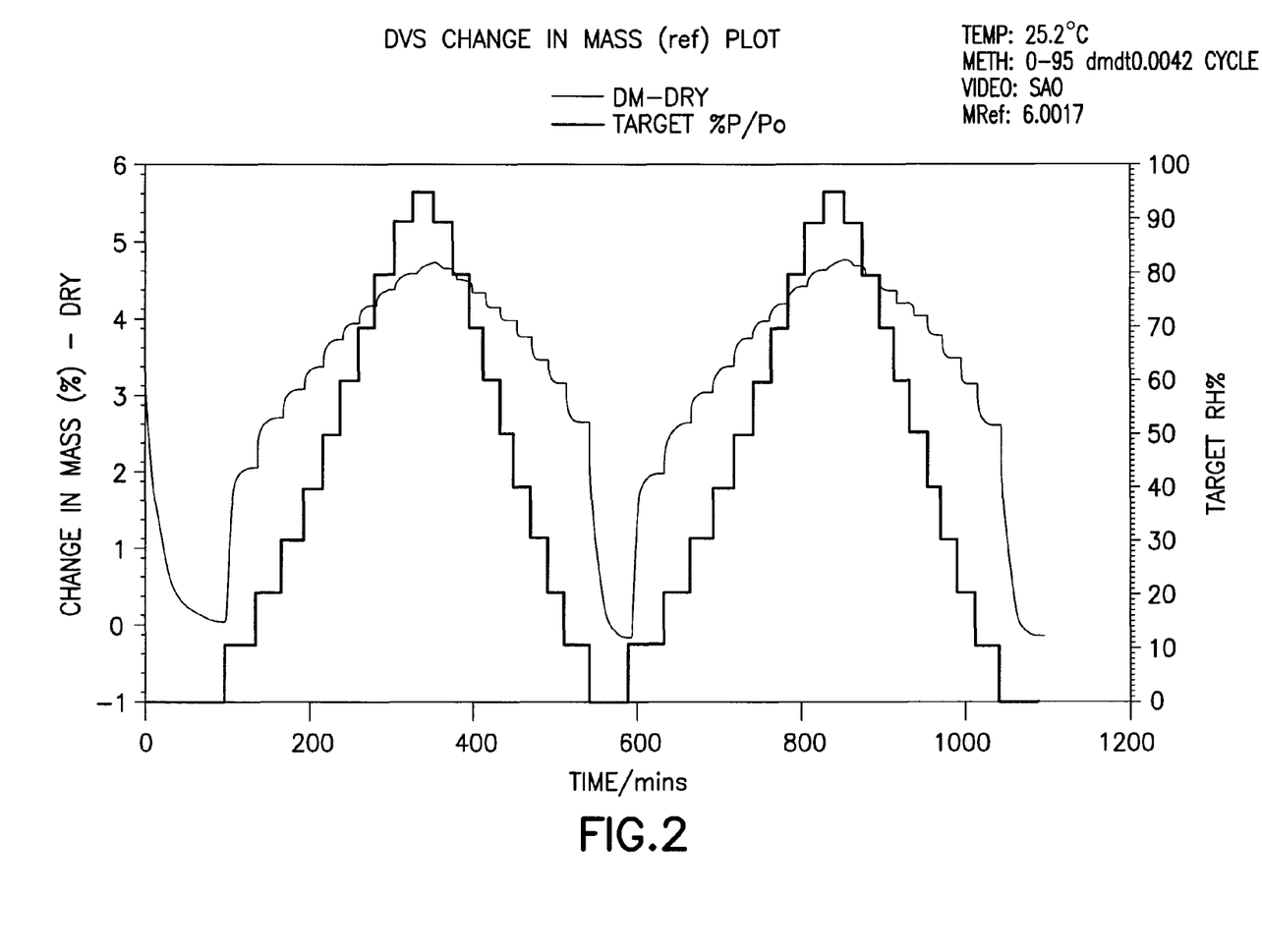
FIG. 2 shows the DVS graph of the crystalline form isolated from slurry treatment in i-PrOH/MeCN
Figure 3:
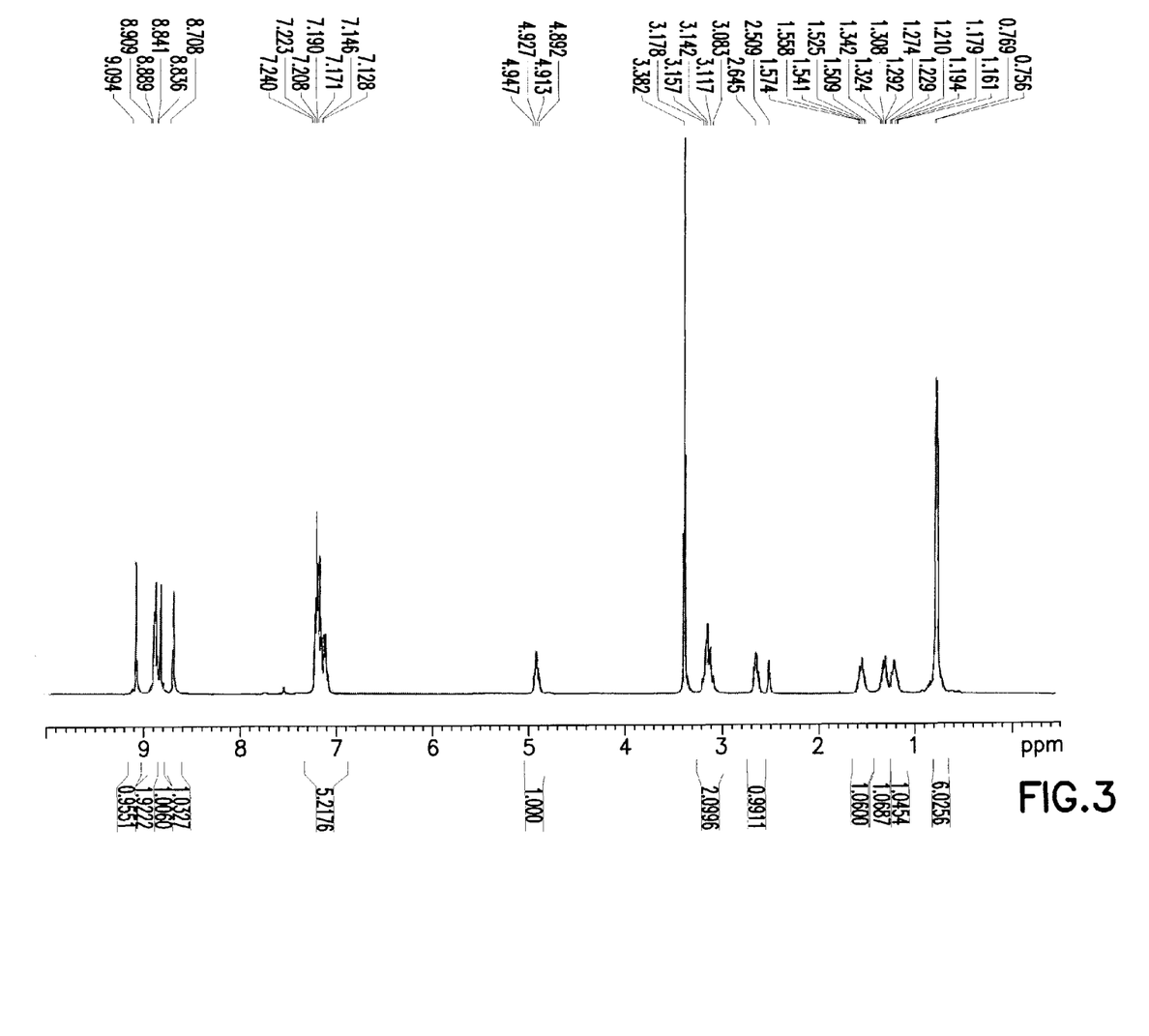
FIG. 3 shows the $^1$H NMR spectrum ($d_6$-DMSO) of the crystalline form, Form C, isolated from slurry treatment in i-PrOH/MeCN
Figure 4:
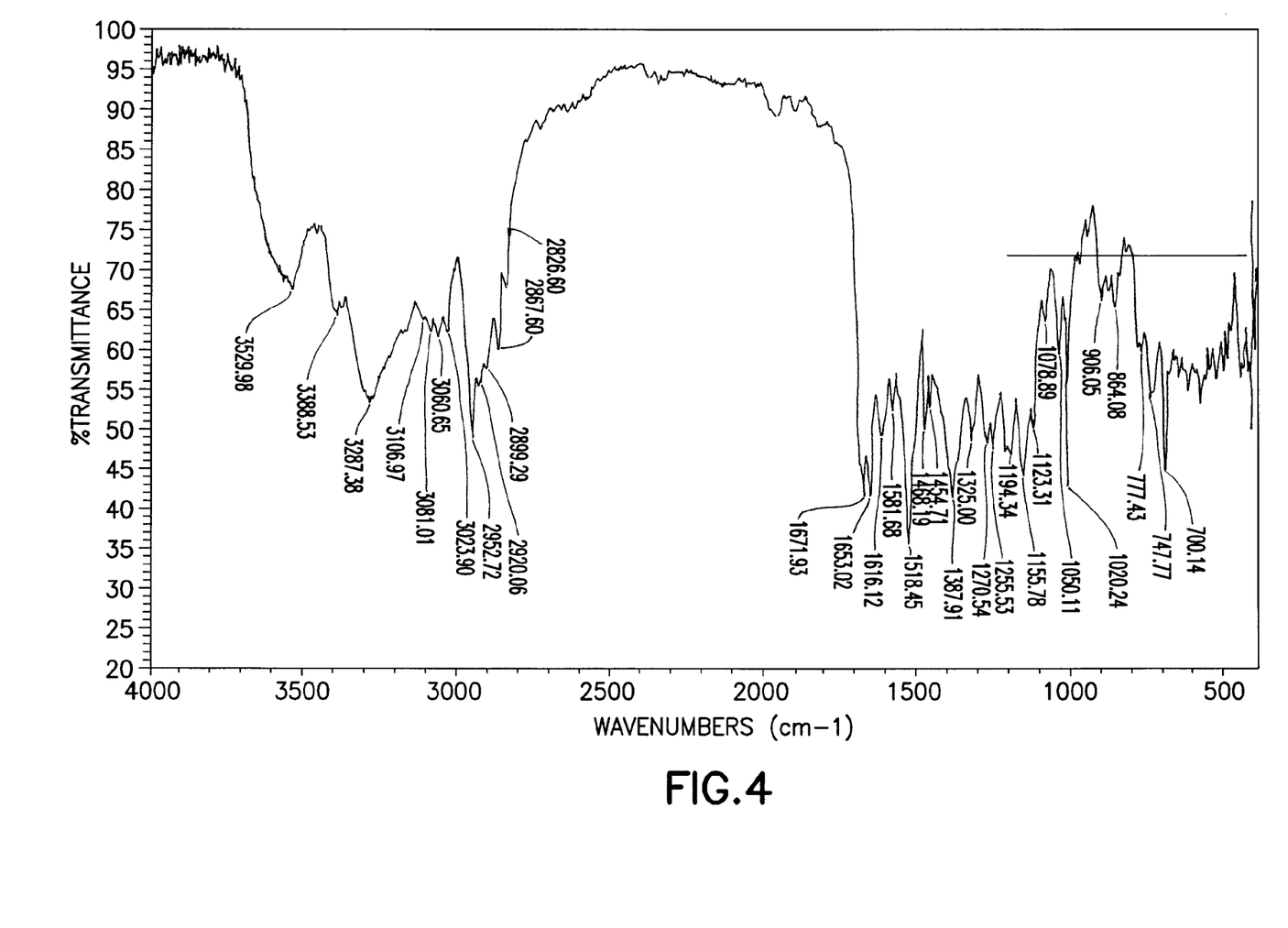
FIG. 4 shows the IR spectrum of the crystalline form, Form C, isolated from treatment slurry in i-PrOH/MeCN
Figure 5:
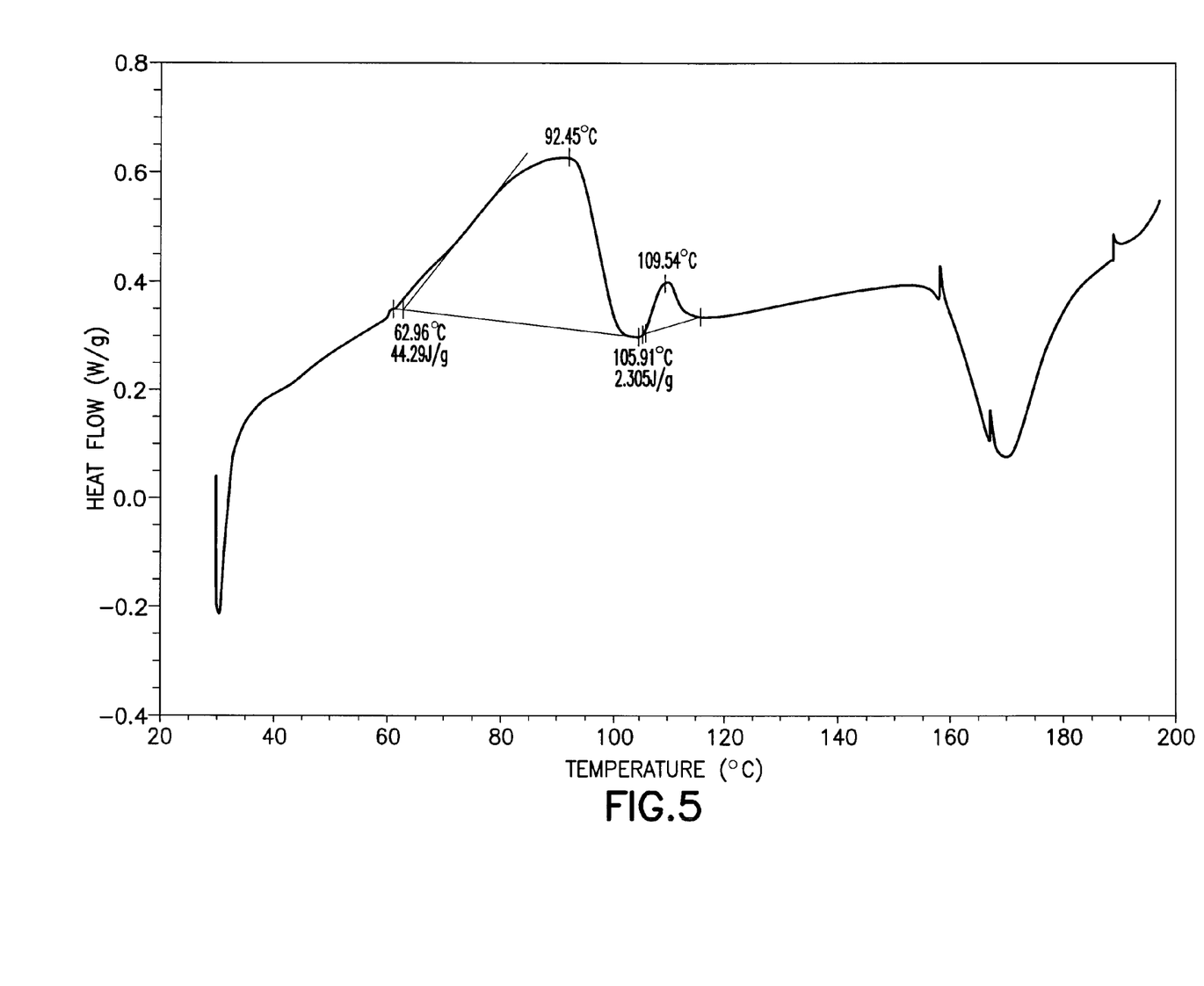
FIG. 5 shows the DSC trace of the crystalline form, Form C, isolated from slurry treatment in i-PrOH/MeCN
Figure 6:
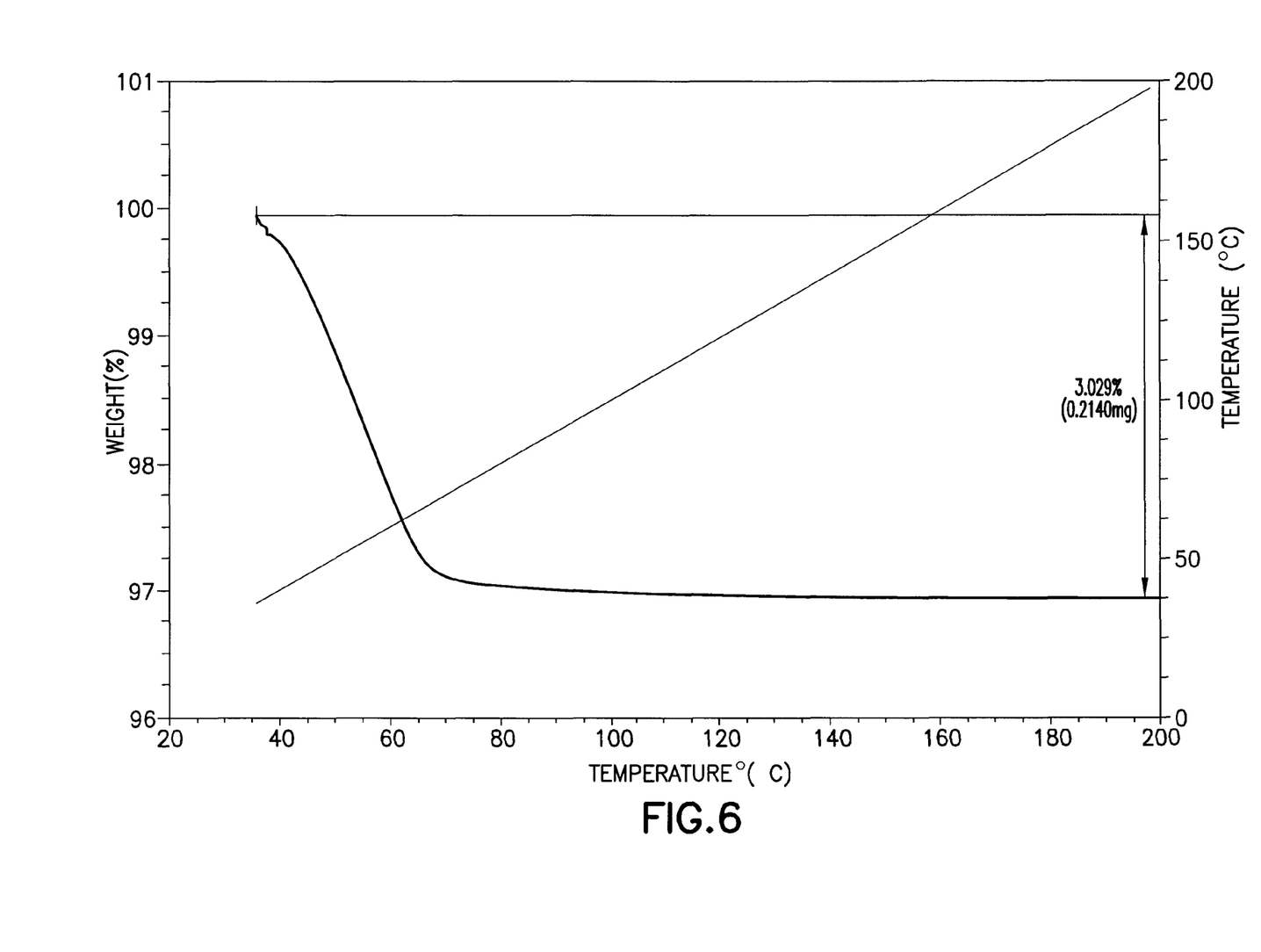
FIG. 6 shows the TGA trace of the crystalline form isolated from slurry treatment in i-PrOH/MeCN

The examples used herein to disclose this embodiment of the invention should not be viewed as limitations and for ones skilled in the art it should be clear that different achiral diols could be used to protected the boronic acid functional group, including diols possessing a larger spacer group between the hydroxy functions, or the use of a non-cyclic system. Furthermore, other salt counter anions could be selected for use in the salt forming step of either [5] or [7] (Scheme 4) leading to different physical properties. Either of these variations or a combination of these variations could provide different solubilities of the desired and undesired stereoisomers which could provide different yields of the desired diastereomers upon isolation.

method produces crystalline bortezomib anhydride (as confirmed by XRPD (X-ray powder diffraction) analysis—see FIG. 1). This crystalline form of bortezomib anhydride provided by this method has the advantageous property of greater stability to storage under protected conditions than crude bortezomib. DVS (dynamic vapor sorption) analysis shows that the crystalline form is slightly hygroscopic but that water absorption is reversible (can absorb or de-absorb water by about 4.5% by weight; FIG. 2).

The purification method to obtain the crystalline form comprises stirring a slurry of bortezomib anhydride in a solvent, preferably MeCN, with or without a co-solvent (preferably i-PrOH), at about ambient temperatures, preferably at about 25° C. In the context of this invention the term slurry means a mixture comprising a heterogeneous mixture composed of a liquid phase at least partially comprising a liquid with a solvating property and a solid phase. This method of producing the crystalline form has been demonstrated for bortezomib anhydride that was shown by XRPD analysis to be of the crystalline form referred to as polymorphic form B (as the polymorphic form is named in WO2009036281 A2). The impurities are extracted from the solid phase of the slurry into the solution phase and a novel crystalline form (Form C) can be obtained by filtration of the slurry. Crystallisation of the slurry purified bortezomib from a second solvent or solvent mixture, preferably EtOAc, gives API grade bortezomib that meets the quality requirement of drug substances as described in the International Conference on Harmonisation (ICH) guidelines.

Scheme 4

Analogues of [7]

Second Embodiment

In another embodiment of the invention a method for the purification of crude bortezomib (by crude we mean directly obtained without purification from synthetic routes either reports in the patent literature or described in the First Embodiment of the present invention). The purification When a binary solvent mixture is used for this purification, the volumetric ratio of the MeCN and i-PrOH can be varied and the novel Form C is still obtained. For example, 15:1 volume/volume and also 7:1 volume/volume mixtures of MeCN and i-PrOH can be used to obtain this form from crude bortezomib. This slurry purification process can provide bortezomib anhydride of ≧99.7/0 HPLC purity directly from crude bortezomib anhydride of about 96% HPLC purity. For example, crude bortezomib with a 96.0% HPLC purity with 1.89% of an impurity and smaller amounts of other impurities can be converted into bortezomib of >99.7% HPLC purity with no impurities at >0.10% by HPLC by use of the MeCN/1-PrOH (15:1 volume/volume ratio) reslurry at about 25° C. for about 4 hours.

A $^1$H NMR (nuclear magnetic resonance) spectrum, an XRPD pattern, an IR (infrared spectroscopy) spectrum, DSC/TGA traces (thermogravimetric analysis) and DVS graph of the crystalline form, Form C, isolated from a MeCN/1-PrOH slurry process are shown below in FIGS. 3, 1, 4, 5, 6, and 2 respectively.

The advantage of this embodiment of the purification of crude bortezomib relates to observations made by the inventors that crude bortezomib (e.g., of 90-98% HPLC purity) was unstable under certain laboratory and experimental conditions, but which can be significantly improve by the slurry purification process of the present invention. Conditions that the crude bortezomib was found to be unstabile in include:

i) in solid form when stored at normal ambient temperature (such as 25° C., in the light or in the absence of the light, in air or in the absence of air) for periods of time (significant decomposition occurs within days), or ii) when dried under vacuum at temperatures above normal ambient temperature, such as 60° C., and iii) when dissolved in solvents such as EtOAc at temperatures required for its dissolution.

Under these conditions the crude bortezomib can undergo chemical change which results in lower recovered yields of bortezomib. By contrast, recrystallisation of bortezomib anhydride, from EtOAc, that had been previously slurry purified as in the process of this embodiment gave improved yields of bortezomib anhydride.

THE ADVANTAGES OF THIS INVENTION

In the first embodiment of this invention, the use of inexpensive achiral diols such as pinacol, in place of the relatively expensive (S)-(+)-pinanediol, for the protection of the boronic acid functional group combined with the use of L-phenylalanine as an internal resolving agent, which is retained in the final API chemical structure, is disclosed. This invention is advantageous in terms of lower reagent cost. Another advantage is that by not utilising a stereochemically pure α-aminoboronic ester, the Matteson homologation chemistry does not have to be conducted under certain conditions which can avoid the epimerisation of the α-chloroboronic ester intermediate (such as [9]). This means that a broader range of reaction conditions and work-up operations can be used that are more convenient for scale up of the synthetic process for the manufacturing plant. This is of importance because U.S. Pat. No. 7,714,159B2 states that the epimerisation of the α-chloroboronic ester intermediate [9], that is an intermediate in the synthesis of bortezomib, was problematic upon scale-up when a solvent swap was required (i.e., when water soluble reaction solvent such as THF had been used) following the reaction prior to aqueous work-up. According to U.S. Pat. No. 7,714,159B2, this epimerisation problem was alleviated by use of MTBE in the Matteson homologation reaction steps because when this solvent was used a solvent swap was not required.

Scheme 5

[9]

The second embodiment of the invention relates to a novel crystalline form of bortezomib that is obtained through a novel method for the purification of bortezomib, namely stirring a slurry comprising crude bortezomib and MeCN or MeCN/1-PrOH at ambient temperature for a suitable period of time. The advantage of this purification method is that it converts crude bortezomib anhydride into a more stable form that is crystalline. Additionally, this method can also comprise a further step of recrystallisation and purification from EtOAc further removing impurities.

EXAMPLES

For embodiment 1, as mentioned previously, the process has been demonstrated using pinacol as the boronate ester diol moiety and the hydrochloride salt of the diastereomeric mixture of [7].

Example 1

Synthesis of [7]

Pinacol 1-chloro-3-methylbutane-1-boronate (rac-[3])

A mixture of THF (2 L) and DCM (55.3 g, 0.651 mol) was cooled to −100° C. n-BuLi (260.7 mL, 2.5 M in n-hexane, 0.651 mol) was added dropwise into the reaction mixture maintaining at −100° C. Pinacol 2-methylpropane-1-boronate ([2]; 100 g, 0.543 mol) was added into the reaction mixture. The resulting mixture was keep at −100° C. for one hour. A solution of ZnCl$_2$ (136.3 g, 1.0 mol) in THF (500 mL) was added dropwise to the reaction over a period of 60 minutes. The resulting mixture was keep at −100° C. for one hour, the reaction mixture was warmed up to room temperature and keep at room temperature overnight. The reaction was diluted with MTBE (750 mL) and was washed twice with saturated NH$_4$Cl (2 L each). The organic layer was dried overnight over MgSO$_4$ before filtering and evaporating. n-Heptane (250 mL) was added into the mixture and was filtered and evaporated providing the product as an oil (119.5 g, 0.514 mol). $^1$H NMR (300 MHz, CDCl$_3$) δ 3.48 (dd, J=9.8, 6.1 Hz, 1H), 1.93-1.71 (m, 2H), 1.61 (td, J=8.1, 4.0 Hz, 1H), 1.33-1.24 (m, 12H), 0.95-0.87 (m, 6H); $^{13}$C NMR (75 MHz, CDCl$_3$) δ 84.5, 42.8, 25.8, 24.8, 23.1, 21.5.

Pinacol 1-bis-(trimethylsilyl)-amino-3-butane-1-boronate (rac-[4])

A solution of LiHMDS (44.61 g, 0.267 mol in 217 mL THF) in THF (750 mL) was cooled to −75° C. and pinacol 1-chloro-3-methylbutane-1-boronate (rac-[3]; 77.5 g, 0.333 mol) in THF (462 mL) was added. The resulting mixture was keep at −75° C. for 1 hour. The reaction mixture was warmed up to room temperature and kept at room temperature overnight. The mixture was evaporated to provide the product as an oil (73 g, 0.204 mol). $^1$H NMR (300 MHz, CDCl$_3$) δ 2.58 (t, J=7.7 Hz, 1H), 1.75 (tq, J=13.1, 6.5 Hz, 1H), 1.66-1.44 (m, 1H), 1.34-1.27 (m, 1H), 1.22 (s, 12H), 0.90-0.84 (m, 6H), 0.12-0.09 (m, 18H).

Pinacol-1-ammonium chloride-3-methylbutane-1-boronate (rac-[5])

A solution of pinacol 1-bis-(trimethylsilyl)-amino-3-butane-1-boronate (rac-[4]; 264.9 g, 0.741 mol) in n-heptane (4 L) and diethyl ether (1.6 L) was cooled to −35° C. HCl gas was bubbled through the mixture for 4 hours, and the resulting mixture was stirred at room temperature overnight and was then filtered. The filter cake was dissolved in DCM (1 L) and was stirred at room temperature for 2.5 hours, filtered and evaporated. The residue was diluted with EtOAc (713 mL) to form a slurry that was stirred for 1 hour and then filtered. The solid was dried under vacuum at 35° C. to provide the product as white crystals (123.9 g, 0.496 mol). $^1$H NMR (300 MHz, d$_6$-DMSO) δ 7.75 (s, 3H), 2.70 (d, J=5.5 Hz, 1H), 1.68 (dt, J=13.5, 6.8 Hz, 1H), 1.44 (t, J=7.3 Hz, 2H), 1.24 (s, 12H), 0.86 (d, J=6.5 Hz, 6H); $^{13}$C NMR (75 MHz, CDCl$_3$) δ 85.0, 38.6, 35.9, 25.1, 24.8, 22.5; ESI-MS (positive) (m/z): 213, 170, 156, 128, 100, 88, 74.

Pinacol N—BOC-L-phenylalanine-D,L-leucine boronate ((R,S)-/(S,S)-[6])

To a cooled (about 0° C.) solution of BOC-L-phenylalanine (60.6 g, 0.228 mol) in DMF (670 mL) was added DIPEA (62.1 g, 0.480 mol), HATU (96.0 g, 0.252 mol) and a DMF (290 mL) solution of rac-[5] (pinacol-1-ammonium chloride-3-methylbutane-1-boronate) (60 g, 0.240 mol). The mixture was warmed to room temperature and stirred at this temperature overnight. Ethyl acetate (1 L) and a saturated aqueous solution of sodium of chloride (700 mL) were added into the reaction mixture. After mixing, the organic layer was separated and washed with a saturated aqueous solution of sodium of chloride (750 mL), then with an aqueous 0.1N solution of KHSO$_4$ (800 mL) and finally with an saturated aqueous solution of NaHCO$_3$ (800 mL). The organic layer was dried over MgSO$_4$ and concentrated at 35° C. n-Heptane (240 mL) was added to the crude product and was stirred for 45 min and was filtered. The filter cake was washed three times with n-heptane (100 mL each) and dried under vacuum at 35° C. The product was obtained as an approximately equimolar mixture of diastereomers as a white solid (92.0 g, 0.200 mol). $^1$H NMR (300 MHz, CDCl$_3$) δ 7.37-7.18 (m, 5H), 6.30 (d, J=31.1 Hz, 1H), 5.07 (s, 1H), 4.45-4.27 (m, 1H), 3.06 (d, J=4.5 Hz, 2H), 2.96 (dd, J=10.8, 8.3 Hz, 1H), 1.39 (s, 9H), 1.37-1.29 (m, 3H), 1.25 (d, J=4.6 Hz, 12H), 0.85 (dt, J=11.3, 5.6 Hz, 6H); $^{13}$C NMR (75 MHz, CDCl$_3$) δ 172.7, 155.6, 136.7, 129.6, 128.9, 127.1, 83.0, 80.4, 54.8, 55.4-53.8 (m), 39.9, 38.5, 37.6, 28.5, 25.7, 25.1, 23.4, 22.0; ESI-MS (positive) (m/z): 461, 405.

Pinacol L-phenylalanine-L-leucine boronate, HCl salt ((R,S)-[7])

A MeCN (752 mL) solution of pinacol N—BOC-L-phenylalanine-D,L-leucine boronate ([6]; 94 g, 0.204 mol) was cooled to about 0° C. HCl gas was bubbled into the reaction mixture for 4 hours. The resulting mixture was stirred at room temperature overnight and was then evaporated to provide a solid. A slurry was formed by the addition of MeCN (250 mL) which was then stirred for 2 hours and was filtered and washed with MeCN (50 mL). The solid was then dried under vacuum at 35° C. furnishing the product as a white solid (56.4 g, 0.136 mol; HPLC purity 96.0% as a 1.5:1 mixture of (R,S)-[7] and (S,S)-[7])).

As mentioned previously the key upgrade step can be accomplished using:
A) fractional crystallisation, or
B) a reslurry/hydrolysis, or
C) chromatography,
D) or combinations of any of the above three techniques
These are exemplified in the following 3 examples.

Example 2

Operation A

Diastereomeric Upgrade of [7] by Fractional Crystallisation

The First Crystallisation

[7] (35.0 g, 88.2 mmol; (R,S)-/(S,S)-diastereomeric ratio=1.50:1) was dissolved in a mixture of isobutyl acetate (350 mL) and ethanol (24.5 mL) at about 75° C. The solution was slowly cooled to ambient temperature and stirred overnight. The resulting mixture was cooled to about 0° C. and stirred for one hour and then filtrated and the isolated solid was dried under vacuum at 35° C. The product was obtained as white solid (12.5 g, 31.5 mmol, HPLC purity 98.61% ((S,R)-[7]+(S,S)-[7]), (S,R)-[7]/(S,S)-[7] ratio of 4.16:1).

The Second Crystallisation

[7] (12.5 g, 31.5 mmol; (R,S)-/(S,S)-diastereomeric ratio=4.16:1) was dissolved in a mixture of isobutyl acetate (125 mL) and ethanol (12.5 mL) at about 75° C. The solution was slowly cooled to ambient temperature and stirred overnight. The resulting mixture was cooled to about 0° C. and stirred for one hour and then filtrated and the isolated solid was dried under vacuum at 35° C. The product was obtained as white solid (7.10 g, 17.9 mmol, HPLC purity 98.58% ((S,R)-[7]+(S,S)-[7]), (S,R)-[7]/(S,S)-[7] ratio of 9.97:1).

The Third Crystallisation

[7] (7.1 g, 17.9 mmol; (R,S)-/(S,S)-diastereomeric ratio=9.97:1) was dissolved in a mixture of isobutyl acetate (71 mL) and ethanol (8.0 mL) at about 75° C. The solution was slowly cooled to ambient temperature and stirred overnight. The resulting mixture was cooled to about 0° C. and stirred for one hour and then filtrated and the isolated solid was dried under vacuum at 35° C. The product was obtained as white solid (5.4 g, 13.6 mmol, HPLC purity 96.69% ((S,R)-[7]+(S,S)-[7]), (S,R)-[7]/(S,S)-[7] ratio of 17.5:1). $^1$H NMR (300 MHz, $d_6$-DMSO) δ 8.71 (d, J=15.6 Hz, 1H), 8.44 (d, 3H), 7.27 (m, 5H), 4.02 (s, 1H), 3.03 (m, 2H), 2.80 (d, J=4.5 Hz, 1H), 1.45 (m, 1H), 1.30-0.95 (m, 14H), 0.97-0.57 (m, 6H); $^{13}$C NMR (75 MHz, CDCl$_3$) δ 168.8, 134.1, 130.2, 129.0, 127.8, 83.7, 53.4, 40.3-36.7 (m), 32.0, 29.3, 25.5, 25.0 (m), 23.4, 22.0; ESI-MS (positive) (m/z): 361, 261.

Example 3

Operation B

Diastereomeric Upgrade of [7] by Slurrying in a Wet Solvent

A slurry of [7] (0.5 g, 1.26 mmol; (R,S)-/(S,S)-diastereomeric ratio=1.30:1) in ethyl acetate (15 mL) containing water (0.05 g, 2.78 mmol) was stirred at room temperature. After 72 hour, a sample was isolated as a white solid by filtration of the slurry and was analysed by HPLC showing a purity 97.7% and a (R,S)-/(S,S)-diastereomeric ratio of 7.0:1.

Example 4

Operation C

Diastereomeric Upgrade of [7] by Chromatography

[7] (1.0 g, 2.52 mmol, (R,S)-/(S,S)-diastereomeric ratio=0.83:1 was dissolved in was dissolved in 1:4 i-PrOH/DCM (5.0 mL) and was purified by silica gel column chromatography eluting with 1:10 1-PrOH/DCM. Three fractions were collection providing 96.7% HPLC purity [7] (0.60 g; (R,S)-[7]/(S,S)-[7]=0.55:1), 97.2% HPLC purity [7] (0.10 g; (R,S)-[7]/(S,S)-[7]=1.98:1), and 95.9% HPLC purity [7] (0.20 g; (R,S)-[7]/(S,S)-[7]=2.25:1), after evaporation of the eluent.

For embodiment 2, examples are provided below.

Example 5

Pinacol N-(pyrazine-2-yl-carbonyl)-L-phenylalanine-L-leucine boronate ((R,S)-[8])

To a cooled (about 0° C.) solution of 2-pyrazinecarboxylic acid (1.61 g, 13 mmol) in DMF (84.6 mL) was added DIPEA (4.74 mL), HATU (5.43 g, 14.3 mmol) and recrystallised pinacol L-phenylalanine-L-leucine boronate HCl salt ((R,S)-[7]; 5.4 g, 13.6 mol, as a 17.5:1 diastereomeric mixture of (R,S)-[7]/(S,S)-[7]). The mixture was warmed to room temperature and was then stirred at this temperature overnight. Ethyl acetate (270 mL) and a saturated aqueous solution of sodium of chloride (260 mL) were added to the reaction mixture. After mixing, the organic layer was separated and washed with a saturated aqueous solution of sodium of chloride (182 mL), then an aqueous 0.1N solution of KHSO$_4$ (273 mL) and finally a saturated aqueous solution of NaHCO$_3$ (182 mL). The organic layer was dried over MgSO$_4$, filtered and evaporated at 35° C. giving the product as white solid (5.77 g, 12.4 mmol; HPLC purity 87.8% ((R,S)-[8]+(S,S)-[8]) as a 22.0:1 diastereomeric mixture of (R,S)-[8])/(S,S)-[8]). $^1$H NMR (300 MHz, CDCl$_3$) δ 9.34 (d, J=1.2 Hz, 1H), 8.72 (t, J=9.9 Hz, 1H), 8.53 (dd, J=2.4, 1.6 Hz, 1H), 8.36 (d, J=8.4 Hz, 1H), 7.26 (ddd, J=10.7, 6.9, 4.8 Hz, 5H), 6.06 (s, 1H), 4.83 (dd, J=14.1, 6.8 Hz, 1H), 3.24-3.15 (m, 2H), 3.06 (dd, J=12.5, 7.4 Hz, 1H), 1.51-1.31 (m, 3H), 1.30-1.22 (s, 12H), 0.83 (t, J=6.7 Hz, 6H); ESI-MS (positive) (m/z): 467.

Bortezomib (anhydride; N-(2-pyrazine)carbonyl-L-phenylalanine-L-leucine boroxine)

1N HCl (37.1 mL) was added dropwise into a mixture of pinacol N-(pyrazine-2-yl-carbonyl)-L-phenylalanine-L-leucine boronate ([8]; 5.77 g, 12.4 mmol as a 22.0 (R,S)-[8])/(S,S)-[8] diastereomeric mixture) and 2-methylpropaneboronic acid (1.89 g, 18.5 mmol) in MeOH (57.7 mL) and n-heptane (57.7 mL). The reaction mixture was stirred at room temperature overnight. The water layer was separated and washed twice with n-heptane (30 mL each). The water layer was concentrated at 35° C. and DCM (30 mL) was added into the residue. 2 N NaOH (36.9 mL) was added dropwise into the reaction mixture. The water layer was separated and washed twice with DCM (30 mL each). After dilution with DCM (30 mL) 1N HCl was added dropwise until the pH of the aqueous phase was about 6. The water layer was extracted twice with DCM (30 mL each). The DCM portions were collected together and concentrated at 35° C. Ethyl acetate (46 mL) was added into the residue and concentrated. Ethyl acetate (16 mL) was added into the residue and concentrated until approximately 10% of the original volume remained. n-Heptane (46 mL) was added and the resulting solid was then filtered, washed with n-heptane (20 mL) and dried under vacuum at 35° C. The crude bortezomib was obtained as yellow solid (3.7 g, 9.63 mmol).

Purification of bortezomib (anhydride; N-(2-pyrazine)carbonyl-L-phenylalanine-L-leucine boroxine), Form C Example 6

A mixture of crude bortezomib (24.2 g, 63.0 mol, HPLC purity: 97.9%), MeCN (181.5 mL) and i-PrOH (12.1 mL) was stirred at room temperature for 4 hours. The solid was filtered and dried at 30° C. under vacuum overnight providing bortezomib anhydride Form C as a white solid (18.6 g, 48.4 mmol, yield 76.9%, HPLC purity: 99.7% with no individual impurity >0.10%).

Example 7

A mixture of crude bortezomib (1.0 g, 2.36 mmol, HPLC purity: 90.7%) and MeCN (8.0 mL) was stirred at room temperature for 6 hours. The solid was filtered and dried at 35° C. under vacuum for 17 hours providing bortezomib anhydride Form C as a white solid (0.75 g, 1.94 mmol, yield 82%, HPLC purity: 99.2%).

Representative XRDP pattern, a DVS graph, $^1$H NMR spectrum, IR spectrum, and DSC and TGA traces of Form C are shown in FIGS. 1, 2, 3, 4, 5 and 6, respectively.

Example 8

Recrystallisation of Bortezomib Anhydride

EtOAc (283.0 mL, 16.0P) was heated to reflux and the bortezomib (17.7 g, HPLC purity: 99.7%) that had been slurry purified in i-PrOH/MeCN as in EXAMPLE 6 was dissolved in the hot EtOAc and then was immediately filtered. The oil-bath was removed, and the filtrate was then allowed to cool to room temperature for 16 hours with stirring. The reaction mixture was cooled to about 0° C. and stirred for 2.5 hours, the solid was filtered and the filter cake was washed with cold EtOAc (35.4 mL, cooled to about 0° C.). The solid was then dried at 30° C. under vacuum for 17 hours giving the rrecrystallised bortezomib anhydride as white crystals (15.2 g, yield: 85.9%, HPLC purity: 99.9%, with no individual impurity >0.10%). $^1$H NMR (300 MHz, CDCl$_3$) δ 9.23 (t, J=2.6 Hz, 1H), 8.68 (dd, J=2.3, 1.3 Hz, 1H), 8.44 (dd, J=2.4, 1.4 Hz, 1H), 8.40 (d, J=8.6 Hz, 1H), 7.28-7.17 (m, 5H), 5.01 (dd, J=15.4, 7.1 Hz, 1H), 3.32-3.11 (m, 2H), 2.91 (s, 1H), 1.55-1.16 (m, 3H), 0.79 (dt, J=16.8, 8.4 Hz, 6H); $^{13}$C NMR (75.45 MHz, CDCl$_3$) δ 172.9, 163.2, 147.8, 144.5, 143.9, 143.0, 135.9, 129.7, 128.9, 127.4, 52.7, 43.6, 40.2, 38.5, 26.1, 23.0 (d, J=28.8 Hz); IR(cm$^{-1}$): 3384, 2954, 2929, 1683, 1515, 1466, 1401, 1386, 1293, 1201, 1020, 702; ESI-MS (positive) (m/z): 1099 [trimeric anhydride]$^+$, 733 [2/3M+H]$^+$, 367 [1/3 M+H−H$_2$O]$^+$.

The invention claimed is:

1. A process of synthesizing bortezomib in its anhydride form of the following formula comprising the steps of:
i) coupling a compound of formula I wherein:
HX is a mineral acid selected from the group consisting of hydrochloric acid, hydrobromic acid, hydroiodic acid, sulfuric acid, phosphoric acid, perchloric acid, and periodic acid; or an organic acid selected from the group consisting of acetic acid, chloroacetic acid, dichloroacetic acid, fluoroacetic acid, difluoroacetic acid, trifluoroacetic acid, benzoic acid, 4-phenylbenzoic acid, 4-chlorobenzoic acid, 4-bromobenzoic acid, tartaric acid, citric acid, malic acid, oxalic acid, malonic acid, 4-methylbenzenesulfonic acid, methanesulfonic acid, trifluoromethanesulfonic acid, camphorsulfonic acid, and a natural amino acid; and the moiety is selected from the group consisting of with an N-protected enantio-enriched L-phenylalanine of the following formula to provide a mixture comprising compounds of formula IV and formula V

-continued

V wherein PO is an N-protecting group selected from the group consisting of tert-butoxycarbonyl (BOC), allyloxycarbonyl (Alloc), benzyloxy-carbonyl (Cbz), 9H-fluoren-9-yl-methoxycarbonyl (Fmoc), triphenylmethyl (Trityl), and dimethoxy)triphenylmethyl (DMTr);

ii) deprotecting the compounds of formula IV and formula V, which are present in the mixture obtained in step i) in the presence of an acid to provide a mixture of a compound of formula II and a compound of formula III

II

III wherein HY is a mineral acid selected from the group consisting of hydrochloric acid, hydrobromic acid, hydroiodic acid, sulfuric acid, phosphoric acid, perchloric acid, and periodic acid; or an organic acid selected from the group consisting of acetic acid, chloroacetic acid, dichloroacetic acid, fluoroacetic acid, difluoroacetic acid, trifluoroacetic acid, benzoic acid, 4-phenylbenzoic acid, 4-chlorobenzoic acid, 4-bromobenzoic acid, tartaric acid, citric acid, malic acid, oxalic acid, malonic acid, 4-methylbenzenesulfonic acid, methanesulfonic acid, trifluoromethanesulfonic acid, camphorsulfonic acid, and a natural amino acid; and iii) resolving the compounds of formula II and formula III, which are present in the mixture obtained in step ii), to provide an enriched compound of formula II,

II iv) reacting the compound of formula II with 2-pyrazinecarboxylic acid in the presence of a base to provide a compound of formula VI

VI and v) converting the compound of formula VI obtained in step iv), in the presence of an acid followed by extraction into dichloromethane (DCM) and concentration and precipitation from EtOAc and n-heptane, to provide bortezomib in its anhydride form.

2. The process according to claim 1 wherein the N-protected enantio-enriched L-phenylalanine is N—BOC-L-phenylalanine.

3. The process of claim 1 where step iii) of resolving comprises crystallisation.

4. The process of claim 1 where step iii) of resolving comprises contacting the mixture of the compound of formula II and compound of formula III with an aqueous organic solvent mixture followed by filtration and isolation of the compound of formula II.

5. The process of claim 1 where step iii) of resolving comprises separation by chromatography.

6. The process of claim 1 where step iii) of resolving comprises exposing the mixture of the compound of formula II and compound of formula III to atmospheric moisture.

7. The process of claim 1 wherein step iii) of resolving comprises recycling the compound of formula III by epimerisation of the chiral center adjacent to the boron atom.

* * * * *